(12) United States Patent
Shah

(10) Patent No.: US 7,667,079 B2
(45) Date of Patent: Feb. 23, 2010

(54) PROCESSES FOR RECOVERY OF A TRIARYLPHOSPHINE FROM A GROUP VIII METAL CATALYST COMPLEX MIXTURE

(75) Inventor: Bakulesh N. Shah, Bay City, TX (US)

(73) Assignee: Oxea Corporation, Dallas, TX (US)

( * ) Notice: Subject to any disclaimer, the term of this patent is extended or adjusted under 35 U.S.C. 154(b) by 536 days.

(21) Appl. No.: 11/112,402

(22) Filed: Apr. 21, 2005

(65) Prior Publication Data

US 2006/0241322 A1 Oct. 26, 2006

(51) Int. Cl.
*C07F 9/02* (2006.01)
(52) U.S. Cl. ........................................ 568/17
(58) Field of Classification Search ............... 568/17
See application file for complete search history.

(56) References Cited

U.S. PATENT DOCUMENTS

| | | | |
|---|---|---|---|
| 4,292,448 A | 9/1981 | Tsunoda et al. | |
| 4,322,564 A | 3/1982 | Tsunoda et al. | |
| 4,503,255 A * | 3/1985 | Booker et al. | 568/17 |
| 4,528,404 A | 7/1985 | Oswald et al. | 568/454 |
| 4,871,879 A | 10/1989 | Laird | |
| 5,110,990 A * | 5/1992 | Blessing et al. | 568/492 |
| 6,335,415 B1 * | 1/2002 | Kelkar et al. | 528/86 |
| 7,196,227 B2 * | 3/2007 | Kanel et al. | 568/9 |

FOREIGN PATENT DOCUMENTS

| | | |
|---|---|---|
| DE | 291223 B1 | 10/1980 |
| GB | 2048862 | 12/1980 |
| JP | 10-291996 | 11/1998 |
| WO | WO 2004/065007 A1 | 8/2004 |

OTHER PUBLICATIONS

Ullmann's Encyclopedia of Industrial Chemistry, M. Bohnet et al., Jan. 15, 2003, Wiley-Vch Verlag GmbH & Co. KGAA, pp. 1-51.

* cited by examiner

*Primary Examiner*—Daniel M Sullivan
*Assistant Examiner*—Chukwuma O Nwaonicha
(74) *Attorney, Agent, or Firm*—Michael W. Ferrell

(57) ABSTRACT

Processes for recovering at least one triarylphosphine from a Group VIII metal catalyst triarylphosphine complex mixture are provided. The processes are particularly useful for recovering the triarylphosphine from spent Group VIII metal catalyst complex mixtures. The processes include the steps of (i) forming a distillate from a Group VIII catalyst complex mixture containing a Group VIII metal catalyst complex, a triarylphosphine, and a light ends component wherein the distillate contains at least a portion of the triarylphosphine as a vapor and at least a portion of the light ends component as a vapor; (ii) cooling the distillate to a temperature below the boiling point of the light ends component to form a condensate; (iii) crystallizing at least a portion of the triarylphosphine using the light ends component as a crystallizing liquid; and (v) recovering the crystallized triarylphosphine from the condensate.

17 Claims, 1 Drawing Sheet

US 7,667,079 B2

PROCESSES FOR RECOVERY OF A TRIARYLPHOSPHINE FROM A GROUP VIII METAL CATALYST COMPLEX MIXTURE

FIELD OF THE DISCLOSURE

This disclosure relates to a process for recovering a triarylphosphine from a Group VIII metal catalyst triarylphosphine complex mixture.

BACKGROUND INFORMATION

Hydroformylation reaction processes, sometimes referred to as "oxo" processes, are widely used commercially to produce aldehydes, such as butyraldehydes. These reaction processes typically involve reacting propylene and synthesis gas ($CO+H_2$) in presence of a Group VIII metal catalyst triarylphosphine complexes. Group VIII metal catalyst triarylphosphine complexes used for hydroformylation can be easily prepared by known methods of forming a complex from compounds of Group VIII noble metals, such as hydrides, halides, carboxylates, nitrates and sulfates, and the triarylphosphine. The Group VIII noble metal compounds and the triarylphosphine may form a complex before introduction into the reaction zone, or alternatively, they can be separately supplied into the reaction zone to form a complex therein. Typical products produced are normal and iso-butyraldehyde.

During the course of the hydroformylation reaction, the Group VIII metal catalyst triarylphosphine complex is periodically removed from the reactor as it accumulates by-products. The removed Group VIII metal catalyst triarylphosphine complexes are collected as "spent" Group VIII metal catalyst triarylphosphine complexes.

In many industrial operations, the Group VIII metal is recovered from the spent catalyst and the triarylphosphine is destroyed during the recovery of the Group VIII metal. Numerous process schemes have been proposed for recovering triarylphosphines from spent Group VIII metal triarylphosphine catalyst complexes. Most processes involve the use of an added solvent to crystallize the triarylphosphines derived from the Group VIII metal catalyst triarylphosphine complexes. For example, U.S. Pat. No. 4,503,255 to Booker et al. discloses subjecting a rhodium catalyst poisoned by the presence of a n-propyldiphenylphosphine to evaporative separation under reduced pressure to separate a vapor containing the n-propyldiphenylphosphine. The distillate is then condensed and the n-propyldiphenylphosphine is recovered by mixing the condensate with a polar solvent and separating the crystalline n-propyldiphenylphosphine from the polar solvent.

Other processes developed for recovering organophosphorus compounds from hydroformylation processes involve removing free organophosphorus compounds from reaction zones and product streams.

U.S. Pat. No. 4,292,448 to Tsunoda et al. discloses a process involving adding an organic solvent to a hydroformylation reaction zone to form a spent catalyst liquid including a Group VIII metal triarylphosphine complex, free triarylphosphine, triarylphosphine oxide. The free triarylphosphine is recovered by cooling the catalyst liquid to selectively crystallize the free triarylphosphine.

U.S. Pat. No. 4,871,879 to Laird discloses a process for isolating rhodium catalyst metals and a triorganophosphine by stripping the overhead of a hydroformylation reactor. The condensate of the overhead is then distilled to recover an aldehyde product in an overhead distillate. The residue remaining after the distillation is then distilled to remove components more volatile than the triorganophosphine to form a heavy ends residue containing the triorganophosphine.

U.S. Pat. No. 5,110,990 to Blessing et al. discloses a process in which a phosphorus ligand is separated from an aldehyde product stream overhead from a hydroformylation reactor. The phosphorus ligand is separated from the aldehyde product stream by contacting the vapor product stream with a spray of dispersed liquid having a lower boiling point than the higher boiling point aldehyde condensation by-products to condense the vaporized phosphorus ligand.

PCT Published Application WO 2004/065007 A1 to Sasol Technology Ltd. discloses a process for recovering an active catalyst component from a hydroformylation process stream. The process stream may be the hydroformylation process heavies purge steam. The active catalyst component may be recovered by mixing a $C_1$ to $C_{10}$ alcohol stream with the process stream. The catalyst component is recovered from a resulting alcohol-rich phase.

SUMMARY OF THE DISCLOSURE

This disclosure relates to processes for recovering at least one triarylphosphine from a mixture containing a Group VIII metal catalyst triarylphosphine complex and free triarylphosphine. The processes are designed to recover the free triarylphosphine from the mixture through distillation and crystallization in the light ends followed by recovery of the triarylphosphine crystals from the condensate of the distillate. The processes eliminate the need for added solvent for purposes of crystallizing and recovering triarylphosphines from a catalyst mixture.

The processes described herein include the steps of (i) forming a distillate from a Group VIII catalyst complex mixture containing a Group VIII metal catalyst complex, a triarylphosphine, and a light ends component wherein the distillate contains at least a portion of the triarylphosphine as a vapor and at least a portion of the light ends component as a vapor; (ii) cooling the distillate to a temperature below the boiling point of the light ends component to form a condensate; (iii) crystallizing at least a portion of the triarylphosphine in the condensate; and (v) recovering the crystallized triarylphosphine from the condensate.

The processes are useful to provide efficient recovery of triarylphosphines from spent Group VIII metal catalyst systems without the need to add a solvent to crystallize the triarylphosphines. The light ends component present in the Group VIII metal catalyst complex mixture serves as crystallizing solvent for crystallization of the triarylphosphine. The mixture containing the Group VIII metal catalyst complex also typically contains a heavy ends component, a portion of which, may be present in the distillate containing at least a portion of the triarylphosphine and at least a portion of the light ends component.

DETAILED DISCLOSURE

Figure 1:
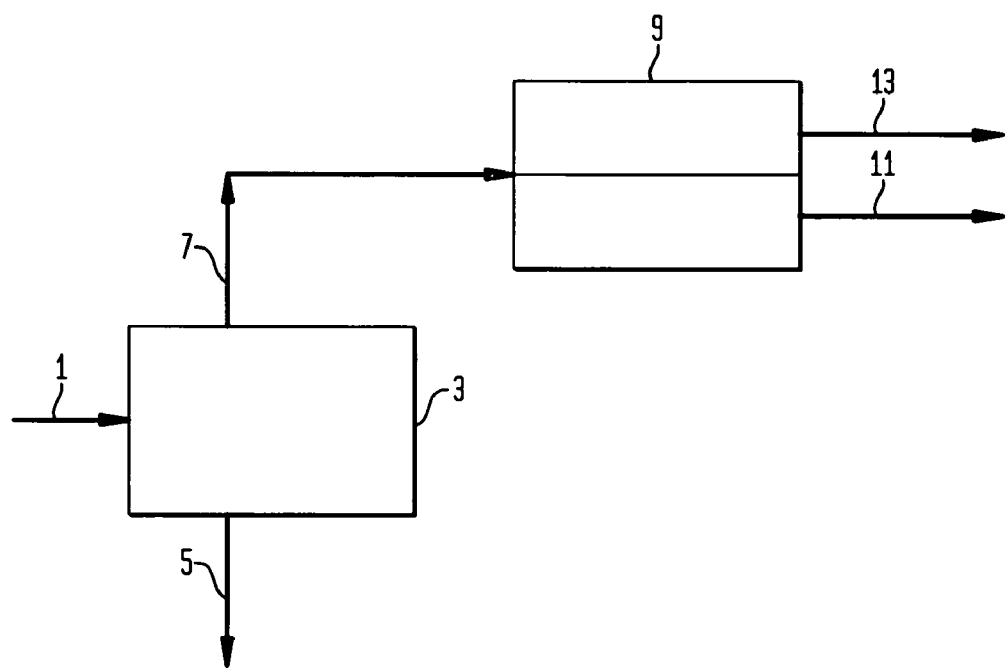
FIG. 1 is a schematic representation of an exemplary process for recovering triarylphosphines in accordance with the processes described herein.

This disclosure relates to processes for recovering at least one triarylphosphine from a Group VIII metal catalyst complex mixture. The processes are designed to recover the triarylphosphine from the Group VIII metal catalyst complex mixture without the use of an added solvent. The processes described herein involve recovery of the triarylphosphine through distillation and crystallization of the triarylphosphine from a liquid. The liquid is derived from components in typical Group VIII metal catalyst complex mixtures. Therefore, the processes described herein eliminate the need for an added solvent for purposes of producing a crystallization liquid. The processes described herein provide for crystallization and recovery of the triarylphosphine from a crystallization liquid that is substantially free of added solvent. For purposes of this disclosure, the term substantially free of added solvent means that added solvent is present in the liquid at concentrations of less than 1 wt. % of the crystallization liquid. In certain embodiments, the crystallization liquid contains no added solvent.

Spent Group VIII metal catalyst triarylphosphine complexes from hydroformylation processes, as indicated by gas chromatographic analysis, are typically part of a mixture containing the Group VIII metal triarylphosphine catalyst complex, free triarylphosphines, and several components other than the Group VIII metal catalyst complex and the free triarylphosphine. The Group VIII metal catalyst complex mixture typically comprises from about 50 ppm to about 5,000 ppm by weight of the Group VIII metal. Each Group VIII metal atom in the Group VIII metal catalyst complex is generally complexed with three molecules of a triarylphosphine. Therefore, the weight percentage of the triarylphosphine in the Group VIII metal catalyst complex mixture in the form of a complex is generally very small. However, in order to efficiently carry out hydroformylation reaction processes, a much larger weight percentage of the triarylphosphine is typically present in the reaction mixture in the form of free triaryphosphine rather than complexed with the Group VIII metal. Typically, the free triarylphosphine is present at a concentration of about 10 wt. % to about 80 wt. % of the Group VIII metal catalyst complex mixture. The processes herein are generally directed to the recovery of this free triarylphosphine from the Group VIII metal catalyst complex mixture.

It is believed that the processes described herein generally do not separate the triarylphosphine from the Group VIII metal catalyst complex to form additional free triarylphosphine. However, to the extent that additional free triarylphosphine is generated from the Group VIII metal catalyst complex, the processes described herein may recover all or a portion of this additional free triarylphosphine.

Many of the components in the Group VIII metal catalyst complex mixture, other than the Group VIII metal complex and the triarylphosphine, are derivatives of the aldehyde product or the triarylphosphine. Some of these components boil at temperatures lower than the boiling temperature of the triarylphosphine and some of the components boil at temperatures higher than the boiling point of the triarylphosphine.

The lower boiling components in the Group VIII metal catalyst complex mixture are referred to as light ends compounds. Exemplary light ends compounds are aldol and Tischenko esters. For purposes of this disclosure, all or any portion of the light ends compounds in the Group VIII metal catalyst mixture shall be collectively referred to as a light ends component. In certain embodiments, the Group VIII metal catalyst complex mixture includes from about 10 wt. % to about 70 wt. % of the light ends component. In other embodiments, the Group VIII metal catalyst complex mixture includes from about 20 wt. % to about 50 wt. % of the light ends component. In still other embodiments, the Group VIII metal catalyst complex mixture includes from about 20 wt. % to about 40 wt. % of the light ends component.

The higher boiling components in the Group VIII metal catalyst complex mixture are referred to as heavy ends compounds. Exemplary heavy ends compounds are reaction products of aldehydes and aryl phosphines. For purposes of this disclosure, all or a portion of the heavy ends compounds shall be collectively referred to as a heavy ends component. In certain embodiments, the Group VIII metal catalyst complex mixture includes from about 5 wt. % to about 70 wt. % of the heavy ends component. In other embodiments, the Group VIII metal catalyst complex mixture includes from about 30 wt. % to about 60 wt. % of the heavy ends component. In still other embodiments, the mixture containing the Group VIII metal catalyst triarylphosphine complex includes from about 40 wt. % to about 60 wt. % of the heavy ends component.

The processes described herein make use of the light ends component in the Group VIII metal catalyst complex mixture to form a distillation condensate in which the triarylphosphine to be recovered is dissolved. In the processes described herein, the triarylphosphine is crystallized from the light ends component by cooling the condensate. Thus, the light ends component acts as a crystallization solvent for the triarylphosphine. The processes described herein are particularly useful for recovering a triarylphosphine from spent Group VIII metal complex mixtures removed from hydroformylation reaction processes, such as for the production of aldehydes.

The processes described herein include the steps of (i) forming a distillate from a Group VIII catalyst complex mixture containing a Group VIII metal catalyst complex, a triarylphosphine, and a light ends component wherein the distillate contains at least a portion of the triarylphosphine as a vapor and at least a portion of the light ends component as a vapor; (ii) cooling the distillate to a temperature below the boiling point of the light ends component to form a condensate; (iii) crystallizing at least a portion of the triarylphosphine from the condensate; and (v) recovering the crystallized triarylphosphine from the condensate.

The distillate may be produced from the Group VIII metal catalyst complex by any suitable means. For example, the distillate may be produced by single or multiple step processes involving heating the Group VIII metal catalyst complex mixture to produce a distillate. The heating processes may take place at a variety of pressures, including reduced pressures. In certain embodiments, the Group VIII metal catalyst mixture in the from of a mixture containing at least a portion of the free triarylphosphine in liquid form, the Group VIII metal catalyst complex, and the light ends component is obtained. The mixture is then subjected to distillation processes.

The mixture containing the liquid triarylphosphine may be obtained by heating a Group VIII metal catalyst complex mixture supply above the melting point of the triarylphosphine. Alternatively, the mixture may be obtained by collecting the Group VIII metal catalyst complex mixture from a hydroformylation reactor system or another source when the mixture is above the melting point of the triarylphosphine. The temperature above the melting point of the triarylphosphine will, of course, vary with identity of the triarylphosphine. Generally, this temperature is from about 60° C. to about 200° C. In certain embodiments, the Group VIII metal complex is heated to a temperature of from about 70° C. to about 150° C. In other embodiments, the Group VIII metal catalyst mixture is heated to a temperature of from about 70° C. to about 100° C.

The processes described herein are useful for recovering a variety of triarylphosphines in Group VIII metal catalyst complex mixtures. Exemplary triarylphosphines are triphenylphosphine; triphenylphosphine having the phenyl group substituted by a methyl or other lower alkyl group, such as tri-p-tolylphosphine, tri-m-tolylphosphine, trixylylphosphine and tris(p-ethylphenyl) phosphine; triarylphosphine having its phenyl group substituted by a methoxy or other alkoxy group, such as tris(p-methoxyphenyl) phosphine; any other triarylphosphine having bonded thereto a substituent which is inert under the hydroformylation conditions; and mixtures thereof. In certain embodiments, the triarylphosphine is triphenylphosphine.

Exemplary Group VIII metals in the Group VIII metal catalyst complex mixtures are selected from rhodium, ruthenium, palladium, osmium, iridium, and combinations thereof. In certain embodiments, the Group VIII metal is selected from the group of rhodium, iridium, and combinations thereof. In other embodiments, the Group VIII metal is rhodium.

In certain embodiments, the Group VIII metal catalyst complex mixture from which the distillate is produced contains from about 10 wt. % to about 80 wt. % of the liquid triarylphosphine, from about 10 wt. % to about 80 wt. % of the light ends component, from about 5 wt. % to about 50 wt. % of the heavy ends component, and from about 50 ppm to about 5,000 ppm of the Group VIII metal. In other embodiments, the Group VIII metal catalyst complex mixture contains from about 20 wt. % to about 80 wt. % of the liquid triarylphosphine, from about 20 wt. % to about 60 wt. % of the light ends component, from about 20 wt. % to about 50 wt. % of the heavy ends component, and from about 100 ppm to about 2,000 ppm of the Group VIII metal. In still other embodiments, the Group VIII metal catalyst complex mixture contains from about 30 wt. % to about 80 wt. % of the liquid triarylphosphine, from about 20 wt. % to about 40 wt. % of the light ends component, from about 40 wt. % to about 50 wt. % of the heavy ends component, and from about 500 ppm to about 1,500 ppm of the Group VIII metal.

The Group VIII metal complex mixture is subjected to evaporative distillation to produce a distillate containing at least a portion of the triarylphosphine and at least a portion of the light ends component. As discussed above, the Group VIII metal catalyst complex mixture containing liquid triarylphosphine may be produced by heating the mixture in the device in which the mixture is subjected to evaporative distillation or by pre-heating in another device prior to entry into the device where the evaporative distillation takes place. Heating to produce the mixture containing the liquid triarylphosphine, in either embodiment, may be conducted in accordance the conditions described above for heating to a temperature above the melting point of the triarylphosphine to form a mixture including triarylphosphine in liquid form.

Suitable evaporative distillation techniques include conventional vacuum distillation, thin film evaporation, and wiped film evaporation, and combinations thereof. In one embodiment, the evaporative distillation technique used is wiped film evaporation.

In certain embodiments, the distillation is conducted at a temperature of about 230° C. to about 315° C. and a pressure of about 0.16 kPa to about 3.3 kPa. In additional embodiments, the distillation is conducted at a temperature of about 240° C. to about 290° C. and a pressure of about 0.18 kPa to about 2.3 kPa. In still other embodiments, the distillation is conducted at a temperature of about 240° C. to about 260° C. and a pressure of about 0.2 kPa to about 0.6 kPa.

In certain embodiments, the distillate contains from about 20 wt. % to about 40 wt. % of the triarylphosphine and from about 60 wt. % to about 90 wt. % of the light ends component. In other embodiments, the distillate contains from about 25 wt. % to about 40 wt. % of the triarylphosphine and from about 65 wt. % to about 85 wt. % of the light ends component. In still other embodiments, the distillate contains from about 25 wt. % to about 35 wt. % of the triarylphosphine and from about 70 wt. % to about 80 wt. % of the light ends component. In certain embodiments, the distillate also contains from about 1 wt. % to about 10 wt. % of a heavy ends component. In other embodiments, the distillate also contains from about 2 wt. % to about 8 wt. % of a heavy ends component. In additional embodiments, the distillate also contains from about 3 wt. % to about 6 wt. % of a heavy ends component.

Generally about 40 wt. % to about 95 wt. % of the Group VIII metal catalyst mixture may be removed in the distillate. However, of course, the amount of the mixture removed as a distillate will depend on the composition of the mixture and the conditions under which the distillation is conducted. Generally, it is found that the processes described herein may be conducted efficiently when the distillation is conducted to the point at which the residue from the mixture distilled contains from about 2 wt. % to about 10 wt. % of the triarylphosphine.

Following distillation, the distillate is cooled, or allowed to cool, to a temperature below the boiling point of the light ends component to form a liquid condensate containing at least a portion of the light ends component in the distillate. At least a portion of the triarylphosphine of the distillate will remain dissolved in the liquid containing the light ends component.

In certain embodiments, the liquid condensate contains from about 70 wt. % to about 95 wt. % of the light ends component and from about 5 wt. % to about 30 wt. % of the dissolved triarylphosphine. In other embodiments, the liquid condensate contains from about 70 wt. % to about 90 wt. % of the light ends component and from about 10 wt. % to about 25 wt. % of the dissolved triarylphosphine. In additional embodiments, the liquid condensate contains from about 75 wt. % to about 85 wt. % of the light ends component and from about 15 wt. % to about 25 wt. % of the dissolved triarylphosphine. In certain embodiments, the liquid condensate also contains from about 1 wt. % to about 15 wt. % of a heavy ends component. In other embodiments, the liquid condensate also contains from about 2 wt. % to about 12 wt. % of a heavy ends component. In additional embodiments, the liquid condensate also contains from about 5 wt. % to about 10 wt. % of a heavy ends component.

In certain embodiments, the condensate compositions will form at a temperature of about 50° C. to about 90° C. In additional embodiments, the condensate will form at a temperature of about 60° C. to about 85° C. In still other embodiments, the condensate will form at a temperature of about 65° C. to about 80° C. In certain embodiments, the liquid condensate is formed by subjecting the distillate to ambient cooling. In other embodiments, the condensate may be formed by actively cooling the distillate.

Upon further cooling, at least a portion of the triarylphosphine will crystallize from the liquid condensate containing the light ends component. In certain embodiments, the crystallization occurs at a temperature of about 0° C. to about 80° C. In other embodiments, the crystallization occurs at a temperature of about 10° C. to about 50° C. In still other embodiments, the crystallization occurs at a temperature of about 20° C. to about 40° C.

The yield of the crystallized triarylphosphine will vary with the weight ratio of the triarylphosphine to the light ends component in the condensate. In some embodiments, the weight ratio of the triarylphosphine to light ends component is from about 1:2 to about 1:5. In additional embodiments, the weight ratio of the triarylphosphine to light ends component is from about 1:2 to about 1:4. In still other embodiments, the weight ratio of the triarylphosphine to light ends component is from about 1:3 to about 1:4.

The cooling of the condensate may be conducted in any known crystallization apparatus by single-stage crystallization or multiple-stage crystallization. In certain embodiments, the crystallization takes place as the condensate is subjected to ambient cooling. In other embodiments, the crystallization takes place as the condensate is actively cooled. For example, the condensate may be cooled by allow the condensate to stand in a vessel at ambient temperature or the vessel may be cooled by circulating chilled water about the vessel or by any other suitable cooling technique.

Generally, the crystallization will proceed until the triarylphosphine concentration dissolved in the condensate reaches its solubility concentration which is dependent on the temperature of the mother liquor. The solubility concentration is generally about 5 wt. % to about 15 wt. % at typical ambient temperatures.

Once crystallized, the triarylphosphine may be recovered by any known technique such as filtration, centrifugal separation, or other techniques. In certain embodiments, the triarylphosphine is recovered by decanting the mother liquor.

An exemplary process of the processes described herein is schematically depicted in FIG. 1. In this process, a stream 1 containing mixture of melted triarylphosphine, a Group VIII metal catalyst complex, a light ends component, and a heavy ends component at a temperature of about 80° C. to about 220° C. is directed to a wiped film evaporator apparatus 3. The stream is subjected to a reduced pressure of about 0.16 kPa to about 3.3 kPa and a temperature of about 240° C. to about 315° C. within the wiped film evaporator. A distillate vapor stream 7 containing the triarylphosphine and the light ends component is withdrawn from the wiped film evaporator 3. A residue stream 5 containing primarily the Group VIII metal catalyst complex and a heavy ends component is removed from the bottom of the wiped film evaporator 3. The distillate stream 7 is directed to a tank 9 where the distillate is allowed to cool to a temperature about 0° C. to about 30° C. by ambient cooling at atmospheric pressure to form a condensate containing the light ends component in liquid form. The triarylphosphine then crystallizes from the condensate. The crystallized triarylphosphine 11 is separated by decanting and may be used in a hydroformylation reaction process. The residual condensate is removed as stream 13 for disposal or for alternative uses such as use as a fuel source.

EXPERIMENTAL EVALUATIONS

The following examples are illustrative of specific embodiments of the processes described herein. All parts and percentages are by weight unless otherwise noted.

Example 1

A sample of a spent Rh-TPP catalyst complex mixture containing 48 wt. % free triphenylphosphine and 20 wt. % of a light ends component was heated to about 90° C. and then flashed in a vacuum flash apparatus at a temperature of 243° C. and a pressure of 0.27 kPa. A residue weighing 10.2% of the original sample weight remained following removal of a distillate. The distillate was allowed to cool through ambient cooling to about 25° C. and crystals weighing 29.7% of the original sample weight were collected from the condensate by decantation. Using gas chromatographic analysis, it was determined that the crystals contained 90.3 wt. % triphenylphosphine. The triphenylphosphine was determined to be suitable for use in a hydroformylation reaction.

Example 2

A sample of spent Rh-TPP catalyst complex mixture containing 29.5 wt. % triphenylphosphine and 30 wt. % of a light ends component was heated to about 90° C. and then flashed in a vacuum flash apparatus at a temperature of 243° C. and a pressure of 0.30 kPa. A residue weighing 8.6% of the original sample weight remained following removal of a distillate. The distillate was allowed to cool through ambient cooling to about 25° C. and crystals weighing 31.3% of the original sample weight were collected from the condensate by decantation. Using gas chromatographic analysis, it was determined that the crystals contained 83.2 wt. % triphenylphosphine. The triphenylphosphine was determined to be suitable for use in a hydroformylation reaction.

Example 3

A sample of a spent Rh-TPP catalyst complex mixture containing 31.4 wt. % triphenylphosphine and 30 wt. % of a light ends component was heated to about 90° C. and then flashed in a vacuum flash apparatus at a temperature of 243° C. and a pressure of 0.30 kPa. A residue weighing 3.7% of the original sample weight remained following removal of a distillate. The distillate was allowed to cool through ambient cooling to about 25° C. and crystals weighing 20.9% of the original sample weight were collected from the condensate by decantation. Using gas chromatographic analysis, it was determined that the crystals contained 84.8 wt. % triphenylphosphine. The triphenylphosphine was determined to be suitable for use in a hydroformylation reaction.

Example 4

A sample of a spent Rh-TPP catalyst complex mixture containing 37 wt. % triphenylphosphine and 30 wt. % of a light ends component was heated to about 90° C. and then flashed in a vacuum flash apparatus at a temperature of 243° C. and a pressure of 0.3 kPa. A residue weighing 53.9% of the original sample weight remained following removal of a distillate. The distillate was allowed to cool through ambient cooling to about 25° C. and crystals weighing 21.9% of the original sample weight were collected from the condensate by decantation. Using gas chromatographic analysis, it was determined that the crystals contained 86.6 wt. % triphenylphosphine. The triphenylphosphine was determined to be suitable for use in a hydroformylation reaction.

Example 5

A sample of a spent Rh-TPP catalyst complex mixture containing 36.4 wt. % triphenylphosphine and 30 wt. % of a light ends component was heated to about 90° C. and then flashed in a vacuum flash apparatus at a temperature of 243° C. and a pressure of 0.26 kPa. A residue weighing 46.1% of the original sample weight remained following removal of a distillate. The distillate was allowed to cool to about 25° C. through ambient cooling and crystals weighing 33.9% of the original sample weight were collected from the condensate by decantation. Using gas chromatographic analysis, it was determined that the crystals contained 88.5 wt. % triphenylphosphine. The triphenylphosphine was determined to be suitable for use in a hydroformylation reaction.

Example 6

A sample of a spent Rh-TPP catalyst complex mixture containing 36.7 wt. % triphenylphosphine and 30 wt. % of a light ends component was heated to about 90° C. and then flashed in a vacuum flash apparatus at a temperature of 240° C. and a pressure of 0.3 kPa. A residue weighing 44.7% of the original sample weight remained following removal of a distillate. The distillate was allowed to cool through ambient cooling to about 25° C. and crystals weighing 40.5% of the original sample weight were collected by decantation. Using gas chromatographic analysis, it was determined that the crystals contained 87.9 wt. % triphenylphosphine. The triphenylphosphine was determined to be suitable for use in a hydroformylation reaction.

With respect to the various ranges set forth herein, any upper limit recited may, of course, be combined with any lower limit for selected sub-ranges.

All patents and publications, including priority documents and testing procedures, referred to herein are hereby incorporated by reference in their entireties.

Although the present invention and its advantages have been described in detail, it should be understood that various changes, substitutions, and alterations could be made without departing from the spirit and scope of the invention as defined by the following claims.

What is claimed is:

1. A process for recovering a triphenylphosphine from a Group VIII metal catalyst complex mixture comprising:
   (i) producing a distillate from a Group VIII metal catalyst complex mixture comprising a Group VIII metal catalyst complex, a triphenylphosphine, and a light ends component wherein the distillate comprises at least a portion of the triphenylphosphine as a vapor and at least a portion of the light ends component as a vapor;
   (ii) cooling the distillate to a temperature below the boiling point of the light ends component to form a condensate comprising from 70 wt. % to 95 wt. % of the light ends component in liquid form and from 5 wt. % to 30 wt. % of the triphenylphosphine;
   (iii) cooling the condensate to a temperature at which at least a portion of the triphenylphosphine is converted to triphenylphosphine crystals in the condensate wherein the condensate is free of an added solvent; and
   (iv) recovering at least a portion of the triphenylphosphine crystals from the condensate.

2. The process of claim 1 wherein the distillate is produced from a mixture comprising a liquid triarylphosphine obtained by heating the Group VIII metal catalyst complex mixture to a temperature above the melting point of the triarylphosphine to form a mixture comprising liquid triarylphosphine, the Group VIII metal catalyst complex, and the light ends component.

3. The process of claim 2 wherein the Group VIII metal catalyst complex is heated to a temperature of 600° C. to 200° C. to form the mixture comprising the liquid triarylphosphine.

4. The process of claim 3 wherein the distillate comprising at least a portion of the triarylphosphine as a vapor and at least a portion of the light ends component as a vapor is formed by subjecting the mixture comprising the liquid triarylphosphine to a temperature of 230° C. to 315° C. and a pressure of 0.16 kPa to 3.3 kPa.

5. The process of claim 4 wherein the condensate is formed by cooling the distillate comprising at least a portion of the triarylphosphine as a vapor and at least a portion of the light ends component as a vapor to a temperature of 50° C. to 90° C.

6. The process of claim 5 wherein the triarylphosphine is selected from the group consisting of triphenylphosphine, tri-p-tolylphosphine, tri-m-tolylphosphine, trixylyl-phosphine, tris(p-ethylphenyl)phosphine, tris(p-methoxyphenyl) phosphine, and mixtures thereof.

7. The process of claim 6 wherein the Group VIII metal catalyst is selected from the group consisting of rhodium, ruthenium, palladium, osmium, iridium, and combinations thereof.

8. The process of claim 7 wherein the triarylphosphine is triphenylphosphine and wherein the Group VIII metal catalyst metal is rhodium.

9. The process of claim 8 wherein the mixture comprising the liquid triarylphosphine comprises from 10 wt. % to 80 wt. % of the triarylphosphine and from 10 wt. % to 80 wt. % of the light ends component.

10. The process of claim 9 wherein the distillate contains from 20 wt. % to 40 wt. % of the triarylphosphine and from 60 wt. % to 90 wt. % of the light ends component.

11. The process of claim 10 wherein the condensate comprises from 70 wt. % to 95 wt. % of the light ends component in liquid form and from 5 wt. % to 30 wt. % of the triphenylphosphine.

12. The process of claim 11 wherein the distillate is formed by subjecting the mixture comprising the liquid triarylphosphine to a temperature of 240° C. to 290° C. and a pressure of 0.18 kPa to 2.3 kPa.

13. The process of claim 12 wherein the condensate is cooled to a temperature of 10° C. to 50° C. to form triarylphosphine crystals in the condensate.

14. The process of claim 8 wherein the mixture comprising the Group VIII metal catalyst triarylphosphine complex, a triarylphosphine, and a light ends component comprises a heavy ends component.

15. The process of claim 14 wherein the distillate comprises at least a portion of the heavy ends component.

16. The process of claim 14 wherein the mixture comprising the liquid triarylphosphine comprises from 20 wt. % to 80 wt. % of the liquid triarylphosphine, from 20 wt. % to 60 wt. % of the light end component; and from 20 wt. % to 50 wt. % of the heavy ends component.

17. The process of claim 11 wherein the condensate comprises from 70 wt. % to 95 wt. % of the light ends component in liquid form; from 5 wt. % to 30 wt. % of the triphenylphosphine; and from 2 wt. % to 12 wt. % of a heavy ends component.

* * * * *